(12) United States Patent
Fernkvist et al.

(10) Patent No.: US 11,672,709 B2
(45) Date of Patent: Jun. 13, 2023

(54) ABSORBENT PRODUCT COMPRISING A NONWOVEN MATERIAL

(71) Applicant: ESSITY HYGIENE AND HEALTH AKTIEBOLAG, Gothenburg (SE)

(72) Inventors: Maria Fernkvist, Gothenburg (SE); Shabira Abbas, Gothenburg (SE); Anna Nihlstrand, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 743 days.

(21) Appl. No.: 15/543,282

(22) PCT Filed: Jan. 14, 2015

(86) PCT No.: PCT/SE2015/050024
§ 371 (c)(1),
(2) Date: Jul. 13, 2017

(87) PCT Pub. No.: WO2016/114692
PCT Pub. Date: Jul. 21, 2016

(65) Prior Publication Data
US 2018/0028372 A1    Feb. 1, 2018

(51) Int. Cl.
*A61F 13/511* (2006.01)
*A61F 13/15* (2006.01)
(Continued)

(52) U.S. Cl.
CPC .. *A61F 13/51113* (2013.01); *A61F 13/15203* (2013.01); *A61F 13/51121* (2013.01);
(Continued)

(58) Field of Classification Search
CPC .......... A61F 13/15203; A61F 13/51113; A61F 13/51121; A61F 13/511; A61F 13/51305;
(Continued)

(56) References Cited

U.S. PATENT DOCUMENTS

| 4,100,324 A | 7/1978 | Anderson et al. |
| 4,377,615 A | 3/1983 | Suzuki et al. |

(Continued)

FOREIGN PATENT DOCUMENTS

| CN | 86107550 A | 7/1987 |
| CN | 1059765 A | 3/1992 |

(Continued)

OTHER PUBLICATIONS

"Beyond." Merriam-Webster.com Dictionary, Merriam-Webster, https://www.merriam-webster.com/dictionary/beyond. Accessed Aug. 10, 2021.*

(Continued)

*Primary Examiner* — Michele M Kidwell
(74) *Attorney, Agent, or Firm* — Buchanan Ingersoll & Rooney PC

(57) ABSTRACT

Absorbent product includes a nonwoven material arranged to be in contact with skin of a user during use of the absorbent product. The nonwoven material includes non-absorbent and/or absorbent fibres. The fibres, at least on a surface arranged to be in contact with skin of a user during use of the absorbent product, have a coarseness of from 0.1 to 10 dtex, or from 0.5 to 7 dtex. The fibres and/or the nonwoven material is coated with a lubricating coating composition suitable for use in absorbent and/or hygiene products at least on a surface arranged to be in contact with skin of a user during use of the absorbent product. By the product including the nonwoven, wet friction can be reduced between the nonwoven and the skin of the user.

19 Claims, 9 Drawing Sheets

(51) Int. Cl.
*A61L 15/42* (2006.01)
*A61L 15/26* (2006.01)
*A61F 13/64* (2006.01)

(52) U.S. Cl.
CPC ............... *A61L 15/26* (2013.01); *A61L 15/42* (2013.01); *A61F 13/64* (2013.01); *A61F 2013/15284* (2013.01); *A61L 2400/10* (2013.01)

(58) Field of Classification Search
CPC ........... A61F 13/64; A61F 2013/15284; A61L 15/26; A61L 15/42; A61L 2400/10; F23N 1/08; F23N 2225/18; F23N 2235/20; F23N 2235/24
See application file for complete search history.

(56) References Cited

U.S. PATENT DOCUMENTS

| | | | |
|---|---|---|---|
| 4,704,112 A | 11/1987 | Suzuki et al. | |
| 5,273,596 A | 12/1993 | Newkirk | |
| 5,383,870 A | 1/1995 | Takai et al. | |
| 5,607,760 A | 3/1997 | Roe | |
| 5,677,028 A | 10/1997 | Ravella | |
| 5,951,535 A | 9/1999 | Fujiwara et al. | |
| 6,087,551 A | 7/2000 | Pereira | |
| 6,115,566 A | 9/2000 | Ohara et al. | |
| 6,120,487 A * | 9/2000 | Ashton | A61F 13/49009 604/358 |
| 6,120,488 A * | 9/2000 | VanRijswijck | A61F 13/494 604/364 |
| 6,531,643 B2 * | 3/2003 | Suzuki | A61F 13/8405 604/381 |
| 6,673,418 B1 | 1/2004 | DeOlivera et al. | |
| 6,740,792 B2 | 5/2004 | Waldroup et al. | |
| 6,803,334 B2 | 10/2004 | Mizutani et al. | |
| 7,297,395 B2 | 11/2007 | Kainth et al. | |
| 7,521,587 B2 | 4/2009 | Busam et al. | |
| 8,022,267 B2 | 9/2011 | Hellstrom et al. | |
| 8,328,782 B2 | 12/2012 | Catalan | |
| 8,637,728 B2 | 1/2014 | Fingal et al. | |
| 8,834,438 B2 | 9/2014 | Kinoshita et al. | |
| 10,022,279 B2 | 7/2018 | Toda et al. | |
| 2001/0053899 A1* | 12/2001 | Mizutani | A61F 13/51121 604/374 |
| 2002/0028624 A1 | 3/2002 | Mizutani et al. | |
| 2002/0052582 A1* | 5/2002 | Takai | A61F 13/512 604/358 |
| 2003/0139711 A1* | 7/2003 | Roe | A61L 15/46 604/367 |
| 2004/0097895 A1 | 5/2004 | Busam et al. | |
| 2004/0158216 A1 | 8/2004 | Kasai et al. | |
| 2006/0121811 A1 | 6/2006 | Mangold et al. | |
| 2009/0155325 A1 | 6/2009 | Wenzel et al. | |
| 2009/0259208 A1 | 10/2009 | Hellstrom et al. | |
| 2010/0191207 A1 | 7/2010 | Oba et al. | |
| 2010/0222757 A1* | 9/2010 | Tee, Jr. | A61F 13/51405 604/367 |
| 2010/0249741 A1 | 9/2010 | Fingal et al. | |
| 2012/0053550 A1 | 3/2012 | Kinoshita et al. | |
| 2017/0367906 A1 | 12/2017 | Abbas et al. | |

FOREIGN PATENT DOCUMENTS

| | | |
|---|---|---|
| CN | 1097450 C | 1/2003 |
| CN | 1518967 A | 8/2004 |
| CN | 1626051 A | 6/2005 |
| CN | 1728979 A | 2/2006 |
| EP | 1184015 A1 | 3/2002 |
| EP | 1444970 A1 | 8/2004 |
| EP | 2401993 A1 | 1/2012 |
| EP | 2401993 B1 | 10/2014 |
| EP | 2957270 A1 | 12/2015 |
| JP | S 54-102095 A | 8/1979 |
| JP | S54-102095 A | 8/1979 |
| JP | H057223 U | 2/1993 |
| JP | H06-078949 A | 3/1994 |
| JP | H08-322876 A | 12/1996 |
| JP | H09-31823 A | 2/1997 |
| JP | H09-117470 A | 5/1997 |
| JP | 2002-065737 A | 3/2002 |
| JP | 2003-052748 A | 2/2003 |
| JP | 2004-512853 A | 4/2004 |
| JP | 2004-255166 A | 9/2004 |
| JP | 2004-305598 A | 11/2004 |
| JP | 2004-344443 A | 12/2004 |
| JP | 2005-534476 A | 11/2005 |
| JP | 2006-519316 A | 8/2006 |
| JP | 2008-529744 A | 8/2008 |
| JP | 2008-529744 A | 8/2008 |
| JP | 2009-030218 A | 2/2009 |
| JP | 2009-110023 A | 5/2009 |
| JP | 2009-532590 A | 9/2009 |
| JP | 2010-527738 A | 8/2010 |
| JP | 2010-200860 A | 9/2010 |
| JP | 2012-518496 A | 8/2012 |
| JP | 2013-40162 A | 2/2013 |
| JP | 2014-155609 A | 8/2014 |
| MX | 2011009038 A | 9/2011 |
| WO | WO-92/00050 A1 | 1/1992 |
| WO | WO-00/38747 A2 | 7/2000 |
| WO | WO-2004/031471 A1 | 4/2004 |
| WO | WO-2006/009995 A1 | 1/2006 |
| WO | WO-2006/069426 A2 | 7/2006 |
| WO | WO-2006/089183 A1 | 8/2006 |
| WO | WO-2007/114742 A1 | 10/2007 |
| WO | WO-2008/147264 A1 | 12/2008 |
| WO | WO-2010/099191 A2 | 9/2010 |
| WO | 2014193279 A1 | 12/2014 |

OTHER PUBLICATIONS

Japanese Office Action dated Oct. 29, 2018 issued in Japanese patent application No. 2017-537252 (6 pages) and its English-language translation thereof (7 pages).
Japanese Office Action dated Oct. 22, 2018 issued in Japanese patent application No. 2017-537249 (5 pages) and its English-language translation thereof (7 pages).
Colombian Office Action Oficio N°. 12944 dated Nov. 25, 2018 issued in Colombian patent application No. NC2017/0007321 (11 pages) and its partial English-language translation thereof (5 pages).
Russian Decision to Grant dated Feb. 28, 2018 issued in related Russian patent application No. 2017128578 (9 pages) and its English-language translation thereof (7 pages).
Russian search report issued in corresponding Russian patent application No. 2017128477 (2 pages) and its English-language translation thereof (2 pages).
Examination report No. 2 dated Feb. 13, 2018 issued in related Australian patent application No. 2015377275 (4 pages).
Japanese Office Action dated Jul. 8, 2019 issued in Japanese patent application No. 2017-537252 (4 pages) and its English-language translation thereof (4 pages).
Decision to Grant dated Apr. 26, 2019 issued in Japanese patent application No. 2017-537249 (4 pages) and its partial machine-translation thereof (2 pages).
Extended European search report dated Jun. 29, 2018 issued in European patent application No. 15878176.5.
Extended European search report dated Sep. 13, 2018 issued in European patent application No. 15878175.7.
Colombian Office Action Oficio N°. 8727 dated Aug. 11, 2018 issued in Colombian patent application No. NC2017/0007321 (12 pages) and its partial English-language translation thereof (6 pages).
Chinese Office Action dated Jan. 10, 2020 issued in Chinese patent application No. 201580073499.1 (8 pages) and its English-language translation thereof (8 pages).
Chinese Office Action dated Jan. 3, 2020 issued in Chinese patent application No. 201580073517.6 (7 pages) and its English-language translation thereof (5 pages).

(56) References Cited

OTHER PUBLICATIONS

Mexican Office Action No. Folio 38715 dated May 17, 2019 issued in Mexican patent application No. MX/a/2017/009206 (3 pages) and its partial English-language translation thereof (2 pages).
Malaysian substantive examination adverse report (Section 30(1)) dated Jun. 25, 2019 issued in Malaysian patent application No. PI 2017702554.
Office Action dated Apr. 2, 2020 issued in U.S. Appl. No. 15/543,266 with double-patenting rejections on pp. 12-15.
Brazilian Office Action dated Apr. 3, 2020 issued in Brazilian patent application No. BR112017012307-0.
Brazilian Office Action dated Apr. 3, 2020 issued in Brazilian patent application No. BR112017013070-0.
Second Chinese Office Action dated Jul. 23, 2020 issued in Chinese patent application No. 201580073499.1 (6 pages) and its English-language translation thereof (8 pages).
Third Chinese Office Action dated Nov. 11, 2020 issued in Chinese patent application No. 201580073499.1 (5 pages) and its English-language translation thereof (5 pages).
Office Action dated Dec. 6, 2020, by the Egyptian Patent Office in corresponding Egyptian Patent Application No. 1120/2017. (5 pages).
Office Action (Notice of Reasons for Rejection) dated Dec. 7, 2020, by the Japanese Patent Office in corresponding Japanese Patent Application No. 2019-202426, and an English Translation of the Office Action. (13 pages).
Office Action dated Jun. 13, 2021, by the Egyptian Patent Office in corresponding Egyptian Patent Application No. 2017071120, and an English Translation of the Office Action. (8 pages).
Office Action dated Dec. 15, 2021, by the Egyptian Patent Office in corresponding Egyptian Patent Application No. 2017071120, and an English Translation of the Office Action. (9 pages).
Office Action issued in Egyptian Patent Application No. 2017071120, dated May 22, 2022, with English Translation (10 pages).
Office Action dated Apr. 25, 2022, by the Brazilian Patent Office in corresponding Brazilian Patent Application No. BR112017013070-0, and an English Translation of the Office Action. (6 pages).
Examination report No. 1 dated Jul. 25, 2017 issued in related Australian patent application No. 2015377275 (3 pages).
Examination report No. 1 dated Jul. 25, 2017 issued in corresponding Australian patent application No. 2015377274 (6 pages).
U.S. Appl. No. 15/543,266, filed Jul. 13, 2017, Shabira Abbas et al.

* cited by examiner

ABSORBENT PRODUCT COMPRISING A NONWOVEN MATERIAL

CROSS-REFERENCE TO PRIOR APPLICATION

This application is a § 371 National Stage Application of PCT International Application No. PCT/SE2015/050024 filed Jan. 14, 2015, which is incorporated herein in its entirety.

TECHNICAL FIELD

Absorbent product including a nonwoven material arranged to be in contact with skin of a user during use of the absorbent product, wherein the nonwoven material includes non-absorbent and/or absorbent fibres.

BACKGROUND

Users of absorbent hygiene products such as diapers, sanitary products or incontinence protection garments, sometimes experience skin problems. Skin problems can be caused by forces arising from physical/mechanical interaction between the product and the user's skin. Thus, for example chafing is caused due to extra friction between the absorbent product and skin of the user. There have been several studies to improve softness of absorbent products and especially nonwoven materials that are used on surfaces in contact with skin, such as topsheets of absorbent products. Today's absorbent products focus on providing products with a high degree of comfort by using nonwoven materials mainly providing a soft feeling towards the skin and this is also disclosed in prior art.

For example WO2008/147264 is related to a nonwoven material for use as a body facing sheet in an absorbent article where the nonwoven material comprises at least two layers where the layer directed against the user during use of the article comprises staple fibres having a coarseness less than 1.5 dtex. This part of the sheet feels soft for the user. It is described that a soft feeling may also be achieved using fibres/filaments such as cotton, viscose, lyocell, having a high softness and textile comfort. However, these fibres/filaments bind liquid and a wet surface against the skin is left, which is not advantageous.

US 2006/0121811 relates to an absorbent product where the surface in physical contact with the skin of the user comprises fine fibres to create a soft material against the skin. Also WO2007/114742 relates to a nonwoven topsheet material comprising microfibres in contact with the skin to improve the softness against the skin.

SUMMARY

It is desired to provide an absorbent product including a nonwoven material arranged to be in contact with skin of a user, which nonwoven material during the use of the absorbent product reduces the risk for mechanical discomfort due to friction between the nonwoven and skin.

We have found that fine fibres with low coarseness, as described in prior art as useful to have closest to the skin to improve the softness, are not necessarily suitable to have closest to the skin of a user of an absorbent product in presence of small amount of moisture. Fine fibres with low coarseness are soft in a dry condition, but when moisture/liquid is present fine fibres also have disadvantages.

Friction occurring between a nonwoven material and the skin of the user is different in the presence of liquid/moisture than when no liquid/moisture is present. Even a very small amount of moisture present originating from perspiration, sweat or other body fluids has an impact on the friction forces occurred between the nonwoven material and the skin of the user. It has therefore been discovered that careful selection of the nonwoven characteristics is able to minimize the mechanical discomfort during the overall use of the product.

It has been realized that one reason for mechanical discomfort is related to "clinging", i.e. forces acting between the absorbent product and the human skin in the presence of moisture (perspiration, sweat, urine). Thus, it is desired to provide an absorbent product with a nonwoven material which minimizes these forces and their negative impact on the skin.

The nonwoven material may be present on all parts of the absorbent product that are in contact with skin, such as for example on topsheet of the absorbent article or in case of a diaper on waist region, hip region, standing gathers, leg openings and belt. The absorbent product provides for low friction between the skin of the user and the product, both when the area is substantially dry but also when the area is moist due to perspiration and sweat or the presence of other bodily fluids. This can be achieved with the absorbent product characterized by the features defined in the appended claims. This can be also attained by the use of an absorbent article, characterized by the features defined in the appended claims.

An embodiment relates to an absorbent product including a nonwoven material arranged to be in contact with skin of a user during use of the absorbent product. The nonwoven material includes non-absorbent and/or absorbent fibres, wherein the fibres at least on a surface arranged to be in contact with skin of a user during the use of the absorbent product have a coarseness of from 0.1 to 10 dtex, from 0.5 to 7 dtex or from 0.5 to 3 dtex. The fibres and/or the nonwoven material can be coated with a lubricating coating composition suitable for use in absorbent and/or hygiene products at least on a surface arranged to be in contact with skin of a user during use of the absorbent product.

The nonwoven material may also include absorbent fibres. The absorbent fibres may have a coarseness from 1 to 10 dtex or from 1.1 to 7 dtex or from 1.2 to 3 dtex.

When using absorbent articles, friction occurs between the skin and the surface of the absorbent article, for example a nonwoven material. The friction between the nonwoven material and skin in presence of moisture/liquid is complex and even a very small amount of moisture has a negative impact on the measured friction. The amount of moisture may be so small that the nonwoven is experienced as dry when touched. In this case, moisture may be present only between the fibres and the skin, each fibre-skin interaction due to the moisture is called a wet contact. The wet contacts are caused by the build-up of menisci between the skin and fibre of the nonwoven in wet contact with the skin.

As mentioned above, one reason for mechanical discomfort is relating to clinging, i.e. the forces acting between the absorbent product and the human skin in the presence of small amounts of moisture such as perspiration, sweat and urine. By understanding the relation between the clinging forces, causing discomfort, and the properties of the nonwoven materials used in absorbent products, it is possible to create a material which minimizes these forces and their negative impact on the skin. Clinging can be described as a perpendicular force acting between a solid material and a support surface in the presence of a small amount of moisture. An example of clinging is a shower curtain which can easily stick to skin in presence of small amount of moisture.

To be able to reduce the friction on areas where nonwoven lies against the skin of a wearer, the nonwoven material should be designed so that at least the wet friction is reduced. Wet friction is experienced between a wet or moist product and skin. Wet friction can occur even at small concentrations of moist or liquid presence in the product or in the boundary between the nonwoven and the skin. Dry friction is experienced between a dry product and skin. The measurement method for determining the wet and dry friction will be described more in detail below.

By coating the nonwoven with a lubricating coating composition suitable for use in absorbent and/or hygiene products at least on a surface arranged to be in contact with skin of a user during use of the absorbent product and having non-absorbent and/or absorbent fibres in the nonwoven having a coarseness of from 0.1 to 10 dtex, from 0.5 to 7 dtex or from 0.5 to 3 dtex. The absorbent product exhibits a reduction in the wet friction between the absorbent product and the skin of a user.

The reduction is achieved by the fact that the lubricating coating composition increases the contact angle, thereby reducing menisci and the wet friction between the skin and nonwoven.

Wet contacts are contacts between the fibres of the nonwoven and the skin, where moisture is present only at the contact points and not in the pores of the nonwoven. A material of coarser fibres renders fewer contact points with skin than a material made of finer fibres. The combination of reducing the number of wet contacts and applying lubricating coating of moisture contributes to reducing the wet friction between the skin of the user and the nonwoven.

The lubricating coating composition may be chosen from silicone oils of which one example is polydimethylsiloxane. These lubricating compositions are non-toxic and provide very good lubricating properties for the absorbent product.

The lubricating coating composition may be coated in an amount of 10 ppm to 10%-by weight, based on the total weight of the nonwoven.

The coating may be applied by means of printing or kiss rolling, where the coating can be applied to 20-100% of the total surface area.

The lubricating coating composition on the nonwoven material may have a water content less than 5.0 weight percent, less than 3.0 weight percent, less than 2 weight percent, less than 1.0 weight percent, or less than 0.5 weight percent. The low water content reduces risk for bacterial growth. To obtain the desired low water content, the coated nonwoven material may be dried after the coating is applied to the nonwoven material.

The nonwoven material may include spunbond, air laid, wet laid, carded, electro spun or meltblown nonwoven or any combination thereof. The nonwoven material may be a laminate or a combination of several types of nonwoven materials. The nonwoven material may include spunbond and meltblown nonwoven in a combination and form a layered product spunbond—meltblown—spunbond (SMS) or spunbond—meltblown—meltblown—spunbond (SMMS).

The nonwoven may have a basis weight from 8 to 80 g/m$^2$, 8 to 40 g/m$^2$ or 8 to 30 g/m$^2$. Thus, a nonwoven material with sufficient basis weight to resist forces created by the friction is provided.

The nonwoven may include a mixture of non-absorbent and absorbent fibres. The absorbent fibres are present in an amount of 2-30% by weight, or about 2-10% by weight, based on the total weight of the fibres in the nonwoven material. The absorbent fibres may have a coarseness from 1 to 10 dtex or from 1.1 to 7 dtex or from 1.2 to 3 dtex.

The absorbent fibres can be based on cellulose including regenerated cellulose fibres such as viscose and/or lyocell fibres which are nontoxic. The non-absorbent fibres may include synthetic fibres, such as polyolefin-based fibres, for example fibres of polypropylene (PP) or polyethylene (PE). The synthetic fibres may be of any commercially available type and can be obtained e.g. by extrusion.

The absorbent product may be a hygienic product with skin contact such as a diaper, incontinence protection garment, sanitary napkin or panty shield. The absorbent product may also be of other type of absorbent product in which a nonwoven is arranged to be in contact with skin of the user.

The absorbent product may include a chassis having a front and rear panel and an absorbent body having a wetting zone for receiving urine and other bodily fluids. The nonwoven material is comprised in at least one region outside the wetting zone in the absorbent body for receiving urine and other bodily fluids. The nonwoven material is alternatively comprised in the regions outside the absorbent body. In case for example diapers, the wetting zone and/or the absorbent body are not always in direct contact with the skin since these areas are distanced from the user by a "cup shape" and/or standing gathers.

The absorbent product may include a waist region, hip region, standing gathers, leg openings and belt. The nonwoven material is at least comprised in at least one of the waist region, hip region, standing gathers, leg openings and belt. These areas may include moisture, e.g. perspiration/sweat, and friction between the nonwoven material and the skin of the user occurs with increased risk for chafing. This risk can be decreased by the use of the nonwoven material in these regions.

The belt can be attached to the chassis or the belt can be separate from the chassis but being arranged to be attachable to the chassis. The nonwoven may at least be comprised in the belt on a side of the belt being arranged to be in contact with skin. Thus risk for chafing and skin problems can be reduced in the belt region.

The absorbent product may include a topsheet, an absorbent body and a backsheet, and wherein the nonwoven material is comprised in the topsheet and/or in the backsheet (for example around the leg openings in the backsheet being in contact with the skin) of the absorbent product. In this way, risk for skin problems can be reduced in a large area of the absorbent product being in contact with the skin.

The nonwoven material as described above can render lower friction values in presence of moisture than a nonwoven material including fibres and/or nonwoven without a coating with a lubricating coating composition and/or fibres having a finer coarseness than 0.1 dtex on a surface arranged to be in contact with skin of a user during use of the absorbent product. These friction values are measured according to a repeated stick and slip method which will be described in more detail below. A curve with friction value measurements is obtained in repeated runs using the method. The curve includes a first slope having a positive coefficient illustrating increase in the friction values, a plateau, and a second slope having a negative coefficient illustrating decrease in the friction values. At the plateau, the friction values are substantially constant over the extension of the plateau. Small variations at the plateau as well as along the slopes are possible between individual values, but with a positive coefficient is meant that all individual values in the first slope together creates a positive coefficient, as well as all individual values in the second slope together creates a negative coefficient, as well as all individual values in the plateau together creates a plateau. Lower friction values render the absorbent product more skin friendly and skin problems arising with the use of the absorbent product can be reduced.

An embodiment relates to an absorbent product including a nonwoven material arranged to be in contact with skin of a user during use of the absorbent product. The nonwoven material has lower friction values in presence of moisture than a nonwoven material including fibres and/or nonwoven without a coating with a lubricating coating composition and/or fibres having a finer coarseness than 0.1 dtex on a surface arranged to be in contact with skin of a user during use of the absorbent product. The friction is measured according to a repeated stick and slip method. A curve with friction value measurements is obtained in repeated runs using the method. The curve includes a first slope having a positive coefficient illustrating increase in the friction values, a plateau, and a second slope having a negative coefficient illustrating decrease in the friction values. Lower friction values render the absorbent product more skin friendly and skin problems arising with the use of the absorbent product can be reduced.

An embodiment relates to an absorbent product including a nonwoven material arranged to be in contact with skin of a user during use of the absorbent product. The nonwoven material has lower maximum friction value in presence of moisture, measured along a curve obtained in repeated runs with measurements according to a repeated stick and slip method, than a nonwoven material including fibres and/or nonwoven without a coating with a lubricating coating composition and/or fibres having a finer coarseness than 0.1 dtex on a surface arranged to be in contact with skin of a user during use of the absorbent product. The friction values are obtained in repeated runs and the obtained friction values during the run form a curve including a first slope having a positive coefficient illustrating increase in the friction values, a plateau, and a second slope having a negative coefficient illustrating decrease in the friction values. The obtained friction values during the run form a curve including a first slope having a positive coefficient illustrating increase in the friction values, a plateau illustrating essentially unchanged friction, and a second slope having a negative coefficient illustrating decrease in the friction values. Lower friction values render the absorbent product more skin friendly and skin problems arising with the use of the absorbent product can be reduced.

An embodiment relates to the use of a nonwoven material in an absorbent or hygiene product to reduce wet friction between the nonwoven material and skin of a user. The nonwoven material includes non-absorbent fibres and/or absorbent fibres, wherein the fibres have a coarseness of from 0.1 to 10 dtex, from 0.5 to 7 dtex or from 0.5 to 3 dtex. The fibres and/or the nonwoven material is coated with a lubricating coating composition suitable for use in absorbent and/or hygiene products at least on a surface arranged to be in contact with skin of a user during use of the absorbent product. It has been surprisingly noted that the nonwoven material of this type with lower friction values render the absorbent product more skin friendly and skin problems arising with the use of the absorbent product can be reduced. The wet friction is measured between the surface of the nonwoven and skin of a user of the absorbent product by the repeated stick and slip method described in the description. The nonwoven material may be used in an absorbent product chosen from a diaper, incontinence protection garment, sanitary napkin or panty shield. The nonwoven material is used in substantially non-absorbent regions of the absorbent product.

Further objects and advantages of the present invention will now be described with reference to the drawings and detailed description below.

DETAILED DESCRIPTION OF PARTICULAR EMBODIMENTS

As used herein, the term "absorbent product" means a product that absorbs or is adapted to absorb bodily fluids, such as urine or blood. The absorbent product is wearable by a user, and, as used herein, the term "wearable absorbent product" means an absorbent article which is to be worn by the user, such as a diaper, pant-type diaper, sanitary napkin, panty-liner or incontinence product.

As used herein, the term "absorbent fibre" means a fibre having the ability to absorb liquid, such as about 1 g liquid/1 g fibres. The fibre also has moisture buffering capacity and is defined as hygroscopic.

As used herein, the term "non-absorbent fibre" means a fibre with substantially no absorption capacity.

The nonwoven material layers or webs may advantageously be spunbond, air laid, wet laid, carded, electro spun or meltblown nonwovens. The nonwoven material may be bonded by multiple techniques, e.g. by needling, hydroentangling, or heat bonding.

The nonwoven material of the disclosed products may be a mixture of natural and synthetic materials or be comprised of only synthetic or natural fibres. Natural fibres are for instance cellulosic fibres or fibres from regenerated cellulose. Synthetic fibres are for instance polyester fibres, polyolefin-based fibres such as polypropylene fibres or polyethylene fibres, and/or the combination thereof or the like.

The nonwoven material may be a combination of several types of nonwoven materials, such as spunbond-meltblown, spunbond—meltblown—spunbond (SMS) type or spunbond—meltblown—meltblown—spunbond (SMMS) type. In an embodiment where several layers of nonwoven are laminated by means of gluing or by ultrasound, only the nonwoven layer lying against the skin is the nonwoven material referred to in the description.

The basis weight for the nonwoven layer can be varied of from 8 to 80 $g/m^2$, from 8 to 30 $g/m^2$, or from 8 to 20 $g/m^2$. When the basis weight is under 40 $g/m^2$, sufficient breathability, drapeability and comfort for the product can be obtained. The basis weight of from 8 to 20 $g/m^2$ has been found to provide best comfort and flexibility while processability of the material is still good.

As used herein, the term "lubricating" or "lubricant" means a substance or composition that serves to lubricate, thus making a surface onto which the composition is applied slippery.

The various nonwoven material layers of the elastic laminate may be of the same or different materials and may have the same, similar or different basis weights. If different materials are selected, an elasticised web is attainable having different surface characteristics across the web. For example, the layers may have different friction properties or different liquid/vapour permeability properties.

Figure 1:
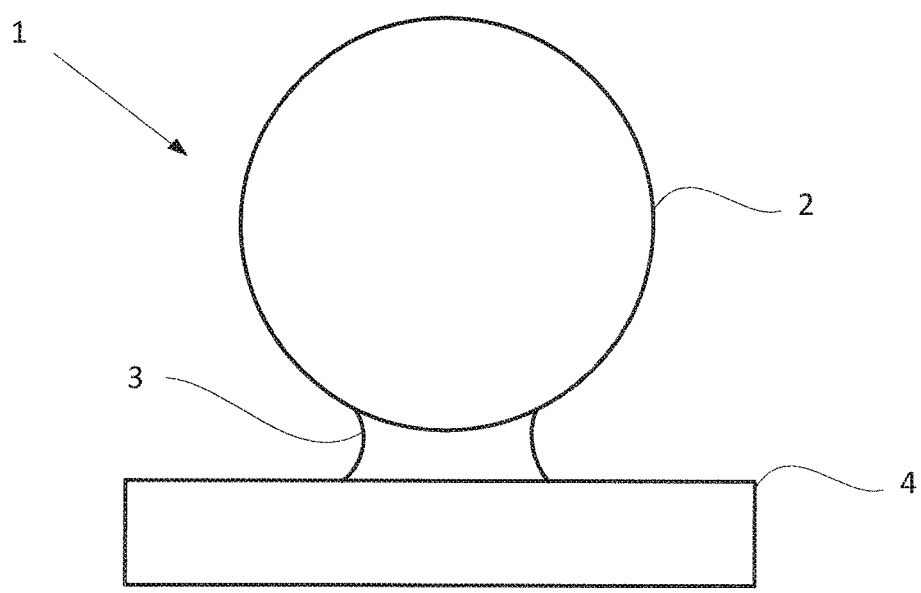
FIG. 1 schematically shows the effect of the presence of moisture on the fibres in a nonwoven when the nonwoven is moist.

The lubricating coating composition may be of the type silicone oil, i.e. polymerized siloxane, and can be polydimethylsiloxane which is also called dimethicone. The water content of the lubricating coating composition may be less than 5.0 weight percent, less than 3.0 weight percent, less than 2 weight percent, less than 1.0 weight percent, or less than 0.5 weight percent. The lubricating composition may be applied to the fibres/the nonwoven material in the form of a liquid solution, but the material is then dried to decrease the water content to less than 5.0 weight percent. FIG. 1 schematically shows the effect of the presence of moisture on the fibres in a nonwoven when the nonwoven is moist.

FIG. 1 schematically shows an enlargement of one fibre 2 in a nonwoven material 1 in the presence of moisture. The moisture causes menisci 3 to form between the fibre and the skin 4 increasing the wet friction between the nonwoven 1 and the skin 4. The menisci 3 form a strong interaction between the nonwoven 1 and skin 4, i.e. that a relatively strong force is needed to break each meniscus 3. This is the effect of the capillarity force of the liquid around the surface contact site (surface contact site is the area of the fibres having contact with the liquid and the area of the skin 4 having contact with the liquid), which can have a profound effect on the strength of adhesion joints and form meniscus 3. When fibres are coated with a lubricating coating composition at least on a surface arranged to be in contact with skin of a user during use of the absorbent product, the lubricating coating composition decreases the wettability of the fibres 2, and the capillarity force is decreased, resulting in that the interaction has been weakened and that a lower force is needed to break each meniscus 3. The lower force needed to break the menisci leads to a reduced wet friction.

Figure 2:
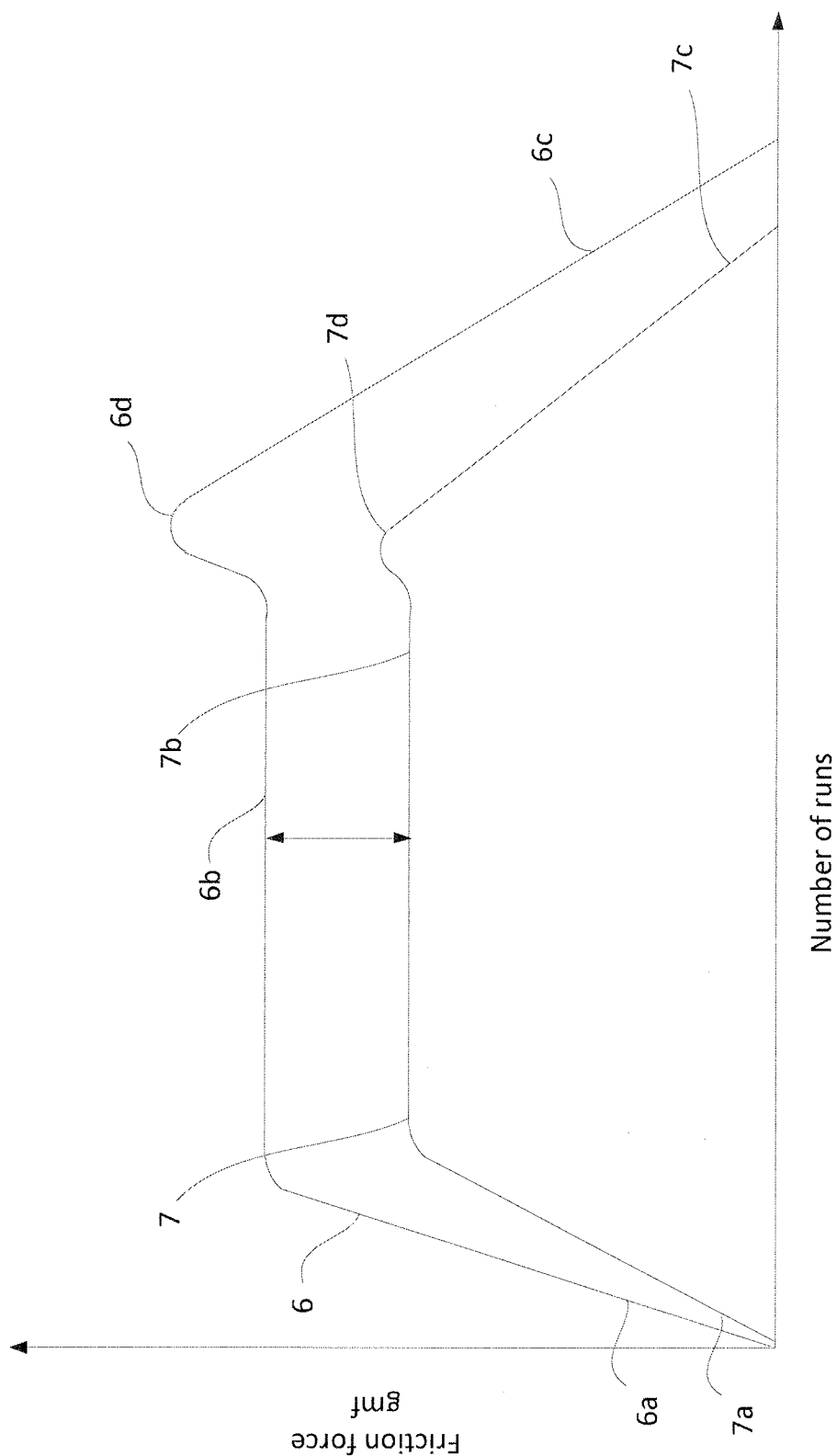
FIG. 2 schematically shows friction measurements made with a nonwoven with and without lubricating coating composition on fibres in a nonwoven using the repeated stick and slip method.

FIG. 2 schematically shows friction measurements made with a nonwoven with and without the lubricating coating composition using the repeated stick and slip method. FIG. 2 includes two curves: first curve 6 illustrating the friction values of a nonwoven including only non-absorbent fibres and second curve 7 illustrating the friction values of a nonwoven including coated fibres. The friction values of curves 6, 7 are plotted in a graph with the number of friction runs on the x-axis and the friction force in gmf on the y-axis. By "gmf" is meant gram-force and one gram-force is 9.80665 mN.

Stick and Slip Measurement Method for Measuring the Wet Friction

The method measures the static friction, sns value (stick and slip value) in gram force, gmf, between a material and the human skin. The method means that repeatedly runs are made using the same material strip. First the sns value for the dry state (dry material and skin) is measured followed by wet state at different liquid levels (from completely wetted material, to moist and to almost dry) until the sns value is back to the skin-material interaction level measured in the first dry run, which means that the material is dry again. The method is thus called a repeated stick and slip method or sns run dry-wet-dry.

Definition of the Method

The stick and slip value is defined as the point on the force curve (gmf) where the material starts gliding over the arm. The sns values from all single force curves are then put together in a new graph, sns values as a function of number of runs.

Principle of the Method

Figure 4A:
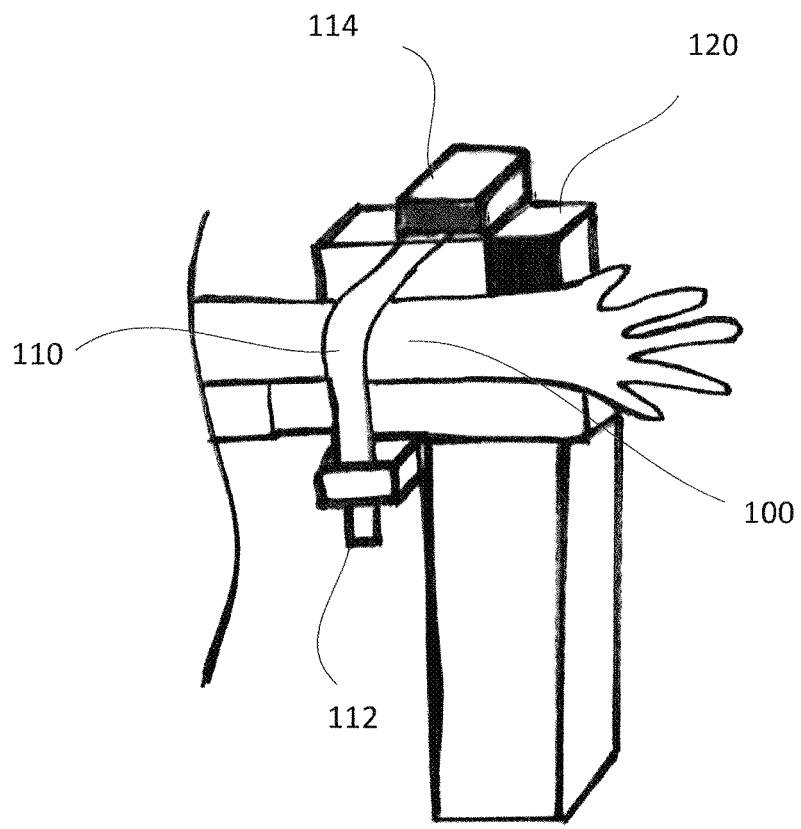
FIG. 4a shows schematically the instrument set up for the stick and slip measurement method.

A strip 110 of test material is pulled, with the help of a MTT 170 tensile tester 120, across the volar forearm 100 to measure the static friction between the material and the skin as illustrated in FIG. 4a. First a dry strip is pulled across the volar forearm. Then the strip is wetted completely and is pulled repeatedly across the volar forearm until the dry state is reached again. Systems with dry skin/dry material, dry skin/wet material, occluded skin/dry material and occluded skin/wet material can be tested. Dry skin/wet material is the only measurement made in the description, however during the wet runs the skin is to a certain degree influenced by the liquid in the system and may become somewhat occluded before finally reaching the level for the dry sns value again.

Equipment of method

Test person's arm, volar forearm

The test person is acclimatized during 15 min in a climate room with 21° C. and 45% rh.

The test is performed in a climate room with 21° C. and 45% rh

MTT 170 tensile tester from DiaStron

Adjustable armrest channel

Software MTT Win (UvWin 1.32.000)

Clamp 1: on the tensile tester

Clamp 2: counter weight, 60 g 0.9 weight % NaCl solution (150 ml/material strip)

Punch, 30×350 mm

Material

The material to be tested is punched or made into rectangular strips measuring 30×350 mm. When testing, the treated side, i.e. the side of the nonwoven having claimed properties, is placed towards the skin.

Wetting of the Material Strip

The material strip is completely wetted by submerging the whole strip in a beaker of 0.9 weight % NaCl solution (150 ml) for 1 min. The strip is lifted in the edge that will be placed in the clamp of the tensile tester using a pair of tweezers. The clamp of the tensile tester is illustrated in FIG. 4a with reference number 114. The strip is slowly pulled up against the edge of the beaker which allows the material to drain its excess liquid. This represents a completely wetted nonwoven, a saturation of 100%. In the other edge of the strip the counter weight of 60 g is placed. The counter weight is illustrated in FIG. 4a with reference number 112.

The sns runs with the wet strip are then tested in the same way as the first run.

Start Procedure

The computer and control unit are turned on and the instrument and program is initialized and is in the ready to start mode.

Delay time is for every friction measurement 12 seconds to give time to zero the load and place the material strip in the right position on the arm before the run begins.

If a material strip has not reached its slip value after 50 mm the distance needs to be increased.

Positioning of Test Persons Arm

The test person should be standing close to the instrument with the arm supported comfortably in the armrest channel. The armrest channel is adjusted so that the top of the volar forearm is in level with the clamp on the tensile tester. This means that the material strip is horizontal between the clamp and arm. During measurements, the arm should be kept still and relaxed.

Performing the Test

The dry nonwoven strip is placed in the clamp on the tensile tester and the 60 g counter weight is fastened in the other edge of the strip.

The test persons arm should be correctly placed in the armrest channel as described according to "Positioning of test persons arm".

The test is started. The first seconds of the delay time is used to zero the measurement, lift the nonwoven strip from the arm and hold the counter weight so that there is no tension on the tensile tester. The nonwoven strip is then hung over the relaxed arm and the counter weight should be still. The sns run starts directly when the delay time of 12 sec. is finished.

The load cell travels the pre-set distance (50 mm) at a certain speed (150 mm/min) and pulls the nonwoven strip over the arm and when it stops the sns value is noted. The so called sns value, which is where the material no longer "sticks" to the skin and starts to glide, is noted for every repetition.

Let the tensile tester go back to the start position.

The same nonwoven strip is then submerged in a bath of 0.9% NaCl solution for 1 min, see instructions about "Wetting of material strip". The wet nonwoven strip is then attached to the clamp on the tensile tester exactly as for the first run with the counterweight in the edge and the arm in the same position. The friction measurement is started in the same way as the first run and the sns value from the friction curve for the second run is noted.

Then the nonwoven strip is lifted away from the arm, without touching anything, while the tensile tester goes back to its start position. When back at the start position the next run will be started, in the same way as for the first run and as soon as possible, and the third sns value is noted. The test continues like this until the sns value is on the same level as the first run.

Calculation and Expression of Results

The sns value from each run is noted (gmf) and a graph showing the repeated sns values (gmf) is made, sns values as a function of number of runs.

Returning to the nonwoven material, the nonwoven material having a lubricating coating composition and wherein the fibres have a coarseness of 0.1 to 10 dtex is represented schematically in FIG. 2 by the second curve 7 and has lower relative friction values than a nonwoven material consisting of fibres without the coating having a finer coarseness than 0.1 dtex represented by first curve 6. The friction values for both materials are measured according to the repeated stick and slip method on the same test person. Curves 6, 7 have friction value measurements obtained in repeated runs using the method. The curves 6,7 comprises a first slope 6a, 7a having a positive coefficient illustrating increase in the friction values, a plateau 6b, 7b and a second slope 6c, 7c having a negative coefficient illustrating decrease in the friction values. At the plateau, the friction values are essentially the same, small variations are possible.

The curves start at a value corresponding to the dry friction measured for dry nonwoven. The positive coefficient of the first slope 6a, 7a indicates an increase in friction when the dry nonwoven is wetted and wet friction occurs. The second slope 6c, 7c illustrates the interface between the skin and nonwoven returning the friction curve to the value of dry friction. As can be seen from FIG. 2, the nonwoven material according to an embodiment of the invention has a lower wet friction over the entire range of runs.

For some materials a very clear peak can be seen in a curve of friction values. As indicated by references 6d and 7d in FIG. 2, these peaks are caused by clinging, which occurs when only a small amount of moisture is present. The mechanical and adhesive properties of many substances are very sensitive to the presence of moisture. This is the effect of the capillarity of liquid around surface contact site, which can have a profound effect of the strength of adhesion joints and form meniscus. This is the clinging effect and clinging force. This clinging value may be reduced with a nonwoven according to embodiments of the invention as the clinging is understood to be mainly caused by the forces acting on the material and the skin by the menisci.

Figure 3:
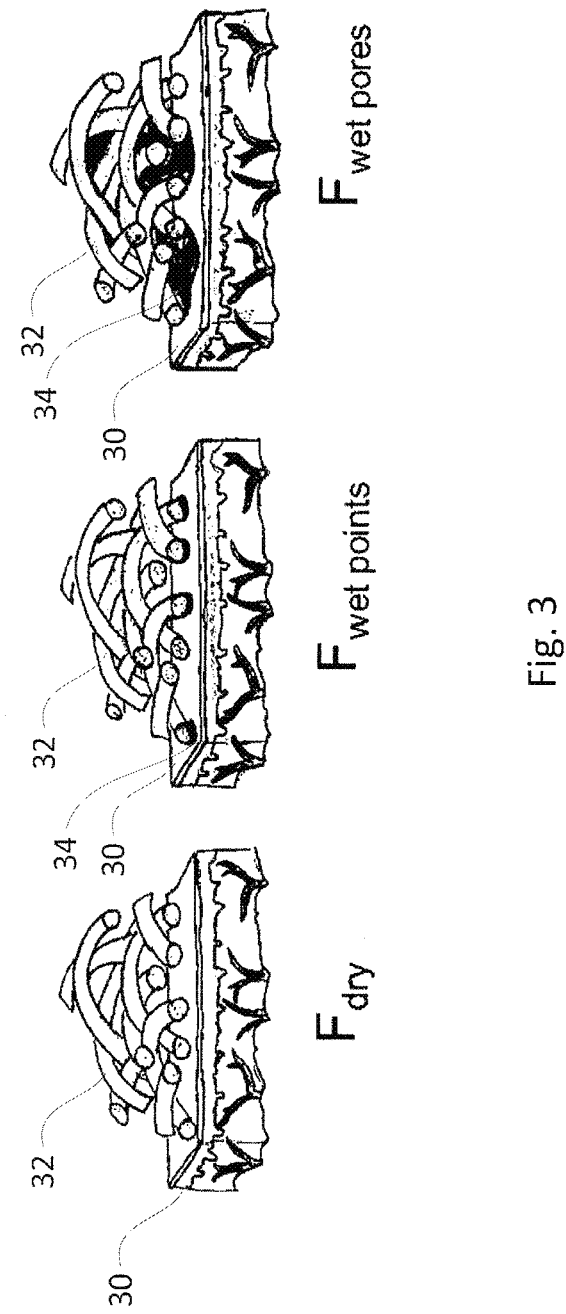
FIG. 3 shows principle sketches of different force contributions.

FIG. 3a shows principle sketches of the different force contributions and where on the wet-dry range they are assumed to act. From left to right: F_dry or the force exerted between dry skin 30 and a dry nonwoven material including fibres 32, Fwet points contacts or the force exerted between the fibres 32 of the material and the skin 30 in the presence of a small amount of moisture 34 and F_wet pores or the force exerted between a wet material including fibres 32 and a large amount of moisture 34 illustrated by the shadowed area and the skin 30. In the last case, there is more moisture present than for when F_wet points contacts is exerted. The larger amount of moisture 34 present in the pores can be seen to create a thin film over the skin.

The total frictional force in a system involving moisture is the sum of the dry force (F_dry) and the clinging force (F_clinging):

$$F\_friction = F\_dry + F\_clinging \quad (Eq. 1)$$

Normally F_dry<<F_clinging. The clinging force can be further divided into contributions arising from wet contacts and wet pores:

$$F\_clinging = F\_wet\ contacts + F\_wet\ pores \quad (Eq. 2)$$

In reality, the frictional force is a mixture of all three interactions occurring in different numbers as described by equation 3:

$$F\_friction(s) = F\_dry \times C\_dry + F\_wet\ contacts \times C\_wet\ contacts(s) + F\_wet\ pores \times C\_wet\ pores(s) \quad (Eq.3)$$

where s is the degree of saturation at the interface and C is the occurrence of interactions.

When the material is wetted, the force from wet pores provides substantial contribution to the wet friction. The wet pore force rapidly increases the friction as seen by the positive coefficient of first slope 6a, 7a of curve as shown in FIG. 2. The material slowly dries over the next runs. Over these runs the force from the wet pores still provides the greatest contribution to the friction force. This is indicated by the plateau 6b, 7b. As the material dries further, the force from the wet contacts, i.e. the menisci described above, provide a sharp rise in the friction force, as indicated by the sharp increase of friction of peak 6d, 7d. After the peak 6d, 7d is reached, the material dries further reducing the number of wet contacts. This quickly returns the curve to the dry friction value. This is seen by the negative coefficient of second slope 6c, 7c. If the peak is reached between two measurements, the peak may not be shown in the measurement.

Figure 4B:
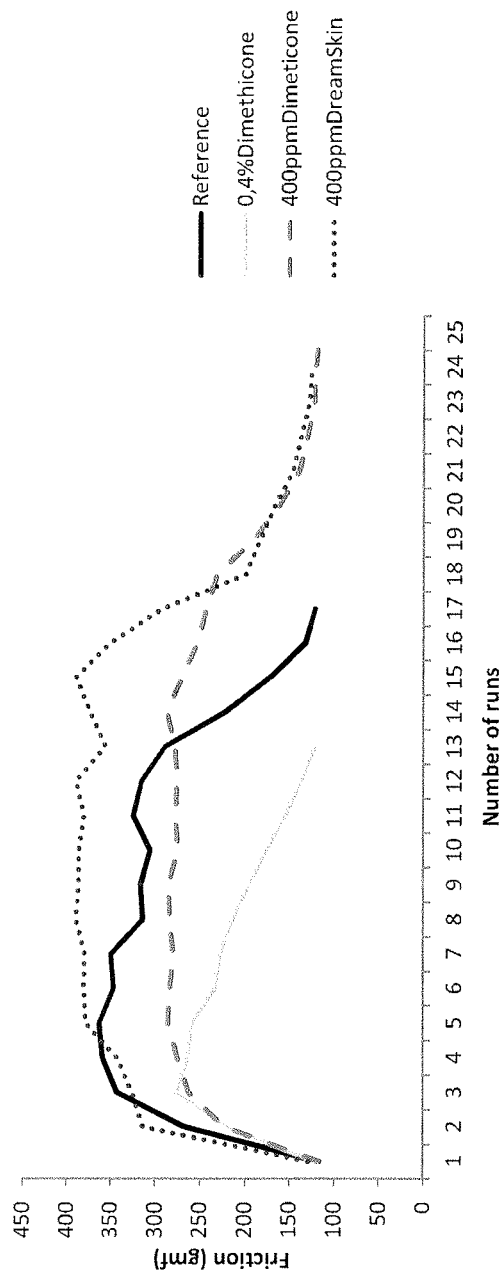
FIG. 4b shows measurement data obtained by the repeated stick and slip method for a number of nonwoven materials including fibres with lubricating coating composition and without lubricating coating composition.

FIG. 4b shows measurement data obtained by the repeated stick and slip method for a reference nonwoven material without a lubricating coating, two nonwoven materials which are the same nonwoven material as the reference, but having a lubricating coating composition dimethicone (PMX-200 Silicone fluid 1.5CS from Dow Corning Corporation) in different amounts, i.e. 400 ppm and 0.4%, respectively and a nonwoven material (also the same nonwoven material as the reference) comprising a coating "Dreamskin" from Intelligent fabrics technology, which is not lubricating. Looking at FIG. 4, overall higher friction values are obtained for the nonwoven without lubricating coating composition (reference curve) whereas lower friction value is obtained for the nonwoven with lubricating coating composition (curve 0.4% Dimethicone and curve 400 ppm Dimethicone). "Dreamskin", which is not a lubricating composition rendered even higher friction values for the nonwoven than the reference without any coating. This illustrates the effect of that applying a lubricating coating composition to the fibres, at least on a surface arranged to be in contact with skin of a user during use of the absorbent, reduces the wet friction. As described in conjuncture with FIG. 2, it can be seen that the plateau level which normally is followed by a sudden increase in friction (the "clinging peak") before the friction force starts to drop again. Table with measurement values for the curves of FIG. 4b can be found in Appendix 1, attached in the end of the detailed description.

An absorbent product generally in which the nonwoven material is used includes a chassis and an absorbent structure within the chassis. The chassis includes a front panel and a rear panel. The front panel is intended to overlie the abdominal region of the wearer and the rear panel is intended to overlie the lower back and buttocks region. The absorbent product also has a crotch region extending between the front panel and the rear panel. The crotch region may be made of the absorbent structure and sometimes also the chassis of the product. Typically, the absorbent structure further includes an absorbent body located primarily in the crotch region but can also extend into the front panel and the back panel of the chassis, with the absorbent body being sandwiched between a liquid previous topsheet and a generally liquid impervious backsheet. The outer cover of the chassis may also be the liquid impervious backsheet of the absorbent structure.

The absorbent body may include any conventional material suitable for absorbing discharged bodily wastes, such as cellulosic fluff pulp, tissue layers, highly absorbent polymers (superabsorbents), absorbent foam materials including hydrogel-foam material, absorbent nonwoven materials or the like.

Generally, the liquid permeable topsheet comprises or consist of a nonwoven material. The topsheet material may further be composed of tow fibres, porous foams, apertured plastic films etc. As mentioned above, the materials suited as topsheet materials should be soft and non-irritating to the skin and be readily penetrated by body fluid, e.g. urine or menstrual fluid, and display low rewetting properties.

The liquid impermeable backsheet may comprise or consist of a thin plastic film, e.g. a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapour to escape from the absorbent body, while still preventing liquids from passing through the backsheet material.

The topsheet and backsheet may be connected to each other for example by adhesive bonding, gluing or welding by heat or ultrasonic. The topsheet and/or the backsheet may further be attached to the absorbent body by any method known in the art, such as adhesive, heat-bonding etc.

Below follows a number of examples of absorbent products including a nonwoven material. The absorbent products are wearable absorbent products. Features of the absorbent articles shared between the products have the same reference numbers. In accordance with an embodiment of the present invention the absorbent product, i.e. for example a conventional diaper, belted absorbent product or pant type diaper or any other absorbent product, includes at least one region including the nonwoven as described earlier. The region can at least partially include a waist region and/or a hip region of the absorbent product to provide comfort and fit around the waist. The hip region is defined as the region below the waist region and above the crotch region. It includes the hips, the abdominal region and the lower part of the back and the upper parts of the buttocks that are at the same height as the hips. The region may also be a leg structure in the crotch region, whereby the nonwoven can provide a reduced friction against the skin of the user when the contact surface includes moisture. The nonwoven may also constitute at least a part of a standing gather structure in the crotch region of the absorbent product or it can be a part of a crotch elastic structure in the crotch region. The crotch elastic structure serves i.a. to encourage the absorbent product to adopt a bowl shape in the crotch region when the product is worn to thereby assist in retaining discharged bodily wastes.

The nonwoven can be especially suitable to be used at regions outside an initial wetting zone or landing zone of the absorbent products. This means that the nonwoven may at least partially cover the absorbent structure, but can be located outside the initial wetting zone or landing zone, i.e. an area in the crotch portion to which urine initially lands.

Figure 5:
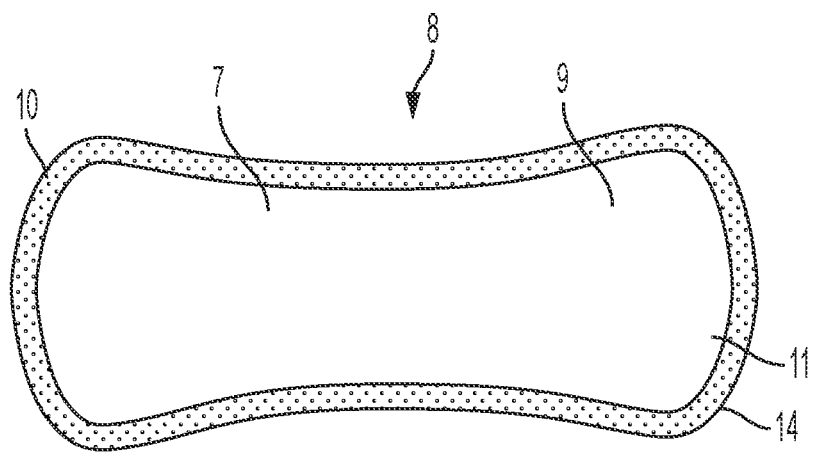
FIG. 5 schematically shows an absorbent article in the form of a panty liner including a nonwoven material.

FIG. 5 schematically shows an absorbent article in the form of a panty liner 8 including a nonwoven. As used herein, the term "panty liner" means an absorbent product which is used for feminine hygiene and which is narrower than sanitary napkins. Panty liners absorb less liquid than sanitary napkins and are thus aimed for light bodily discharge and for everyday cleanliness. The panty liner 8 includes a liquid-permeable topsheet 9, a liquid-impermeable back sheet 10 and an absorbent body 11 arranged between the topsheet 9 and the back sheet 10. The absorbent body 11 includes an absorbent material with absorbent characteristics and a superabsorbent material. The panty liner 8 has a first extension in a longitudinal direction and a second extension in a transverse direction. The panty liner 8 includes a nonwoven having fibres with a coarseness of from 0.1 to 10 dtex, or from 2 to 7 dtex. The fibres and/or the nonwoven material, at least on a surface 14 arranged to be in contact with skin of a user during use of the absorbent product, is coated with a lubricating coating composition suitable for use in absorbent and/or hygiene products, below called lubricating coated nonwoven. This surface 14 can be the entire topsheet 9 or the part of the topsheet which lies outside the absorbent body 11 of the panty liner 8.

Figure 6:
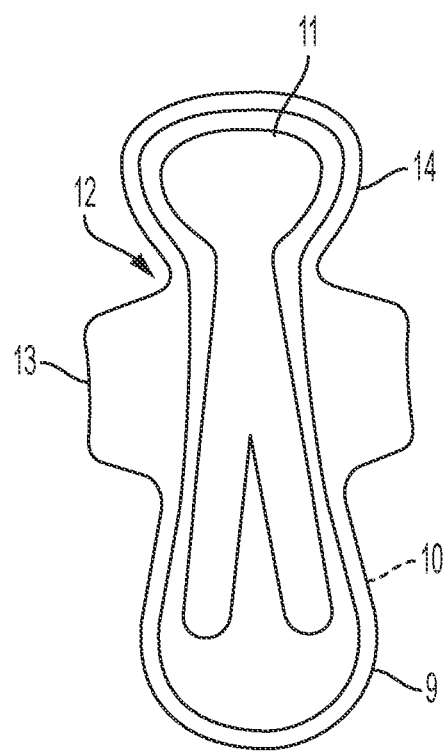
FIG. 6 schematically shows an absorbent article in the form of a sanitary napkin including a nonwoven material.

FIG. 6 schematically shows an absorbent article in the form of a sanitary napkin 12 including a lubricating coated nonwoven according to an embodiment of the invention. The sanitary napkin 12 includes a liquid-permeable topsheet 9, a liquid-impermeable back sheet 10 and an absorbent body 11 arranged between the topsheet 9 and the back sheet 10. The absorbent body 11 includes an absorbent material with absorbent characteristics and a superabsorbent material. The sanitary napkin has a first extension in a longitudinal direction and a second extension in a transverse direction. The sanitary napkin may include wings 13, which are intended to be wrapped around the underwear of a user to secure it properly. The sanitary napkin 12 includes a nonwoven having a mixture of non-absorbent and absorbent fibres, wherein the non-absorbent and/or absorbent fibres have a coarseness of 1 to 10 dtex, at least on the surface 14 of the sanitary napkin 12 which is in contact with the skin. This surface 14 can be the entire topsheet 9 or the part of the topsheet 9 which lies outside the absorbent body 11 of the sanitary napkin 12. The part of the topsheet 9 which lies outside the absorbent body 11 of the sanitary napkin 12 may include the wings 13.

Figure 7:
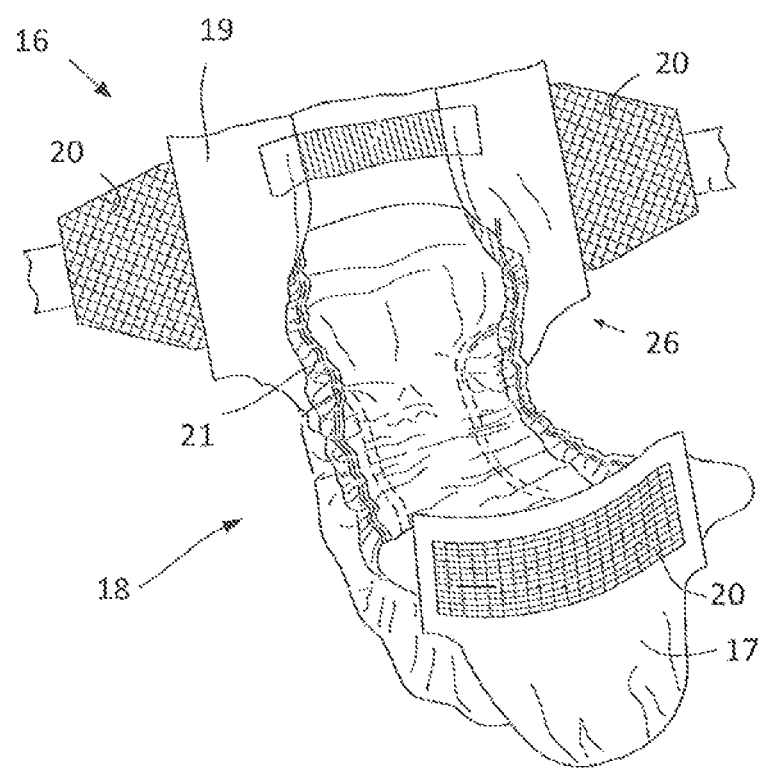
FIG. 7 schematically shows an absorbent article in the form of a diaper including a nonwoven material.

FIG. 7 schematically shows an absorbent article in the form of a diaper 16 including a lubricating coated nonwoven according to an embodiment of the invention. The diaper 16 includes a liquid-permeable topsheet 9, a liquid-impermeable back sheet 10 and an absorbent body 11 arranged between the topsheet 9 and the back sheet 10. The absorbent body 11 includes an absorbent material with absorbent characteristics and a superabsorbent material. The diaper 16 has a first extension in a longitudinal direction and a second extension in a transverse direction. The diaper 16 includes a chassis 26, including a front panel 17, a crotch region 18 and a rear panel 19. An absorbent product in the form of for example a diaper may also include fastening means 20 for securing the front and rear panels 17, 19 to each other to thereby secure the diaper 16 around the waist of a wearer. This type of a diaper is a conventional open diaper. The diaper 16 includes a nonwoven having a mixture of non-absorbent and absorbent fibres, wherein the non-absorbent and/or absorbent fibres have a coarseness of 1 to 10 dtex, at least on the surface of the diaper 16, which is in contact with the skin. This surface can be the entire topsheet 9 or the part of the topsheet 9 which lies outside the absorbent body 11 of the diaper 16. The part of the topsheet 9 which lies outside the absorbent body 11 of the diaper 16 may be part of or the whole of the front panel 17, part of or whole of the rear panel 19 as well as the fastening means 20. A diaper normally includes standing gathers 21 intended to form a leakage barrier to prevent for instance excess fluid from the absorbent body 11 to seep out from the diaper. The standing gathers 21 may also include the lubricating coated nonwoven.

Figure 8:
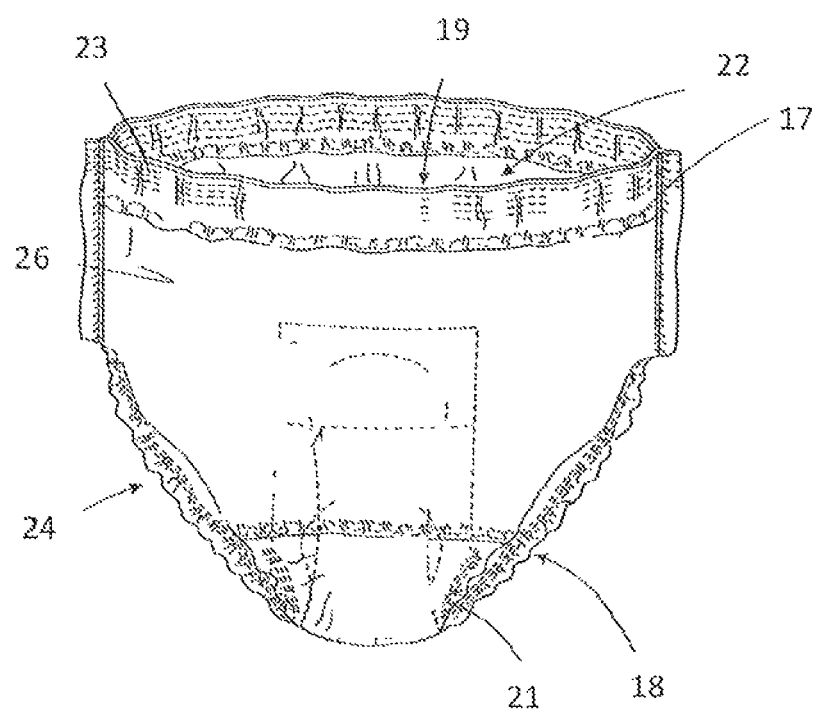
FIG. 8 schematically shows an absorbent article in the form of a pant-type diaper including a nonwoven material.

FIG. 8 schematically shows an absorbent article in the form of a pant-type diaper 22 including a lubricating coated nonwoven according to an embodiment of the invention. In contrast to a conventional open diaper, such as described in conjunction with FIG. 7, the front and rear panels 17, 19 of the chassis 26 of a pant-type diaper are initially secured to each other by means of side seams to thereby provide a garment which can be drawn up on a wearer in the same manner as a normal undergarment. The side seams may be made to be rupturable. The pant-type diaper 22 further includes a waist elastic 23 which is arranged to secure the pant-type diaper around the waist region of the wearer and leg elastic 24 which are arranged to secure the pant-type diaper around the legs of the wearer. The waist elastic 23 and leg elastic 24 may be covered by the lubricating coated nonwoven material. In all other aspects, the pant-type diaper 22 is similar to the diaper 16, and the lubricating coated nonwoven is placed on the same areas as described for the diaper 16.

Figure 9:
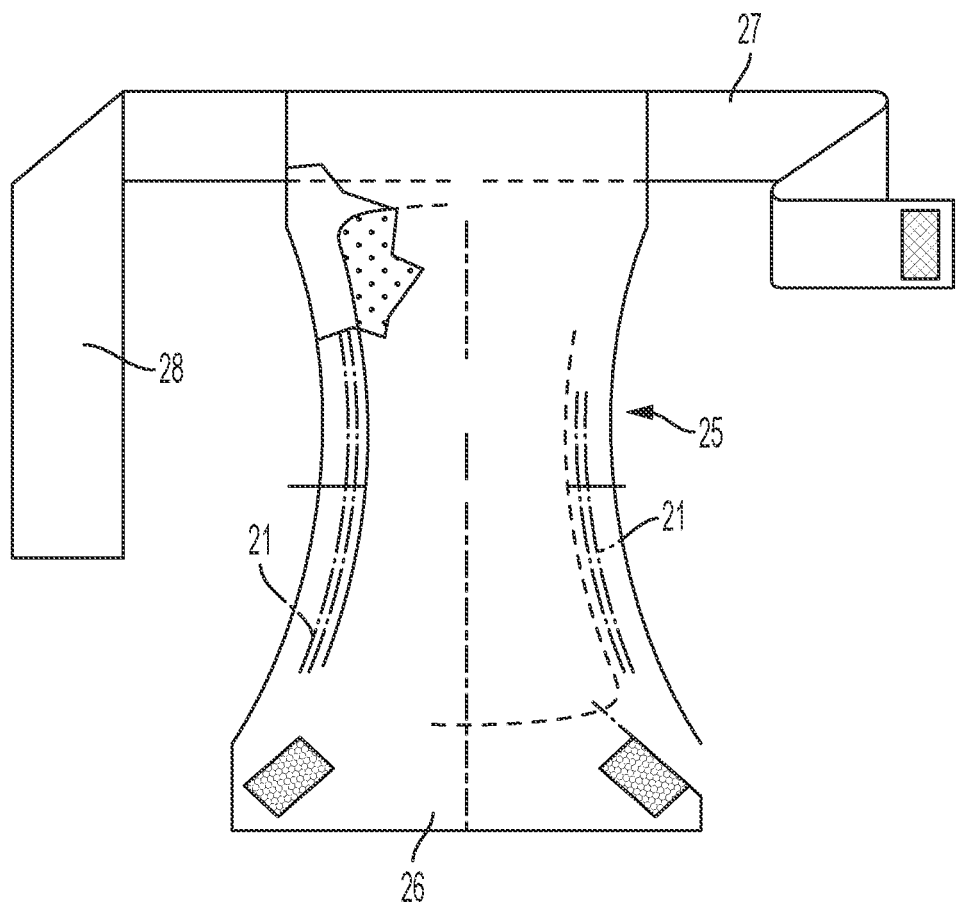
FIG. 9 schematically shows an absorbent article in the form belt-type diaper including a nonwoven material.

FIG. 9 schematically shows an absorbent article in the shape of a belt-diaper 25 including a lubricating coated nonwoven. These products are generally worn by adults and may be adapted for both incontinence and general use. A belted absorbent product is provided with a chassis 26 and two belt halves 27, 28. The chassis of belt-diaper 25 includes a front panel 17, a crotch region 18 and a rear panel 19. The chassis 26 may also include standing gathers 21. The belt halves 27, 28 are either attached to the chassis 26 extending from the lateral sides of the rear panel 19 or are separate from the chassis 26 and arranged to be attached to the chassis 26. The belt halves 27, 28 are intended to be placed around the waist of a wearer and fastened using any suitable fastener to retain the belted absorbent product around the waist of a wearer. Besides the areas of the chassis which may be covered by the lubricating coated nonwoven, the belt on a side of the belt being arranged to be in contact with skin may also include the lubricating coated nonwoven.

The above description defines examples of embodiments of the present invention but is not to be regarded as limiting the invention in any way. The invention may be varied within the scope of the appended claims.

APPENDIX 1

Test results for nonwoven with different coatings or no coating

| number of run | gmf Reference | gmf 0.4% Dimethicone | gmf 400 ppmDimeticone | gmf 400 ppmDreamSkin |
|---|---|---|---|---|
| 1 | 118 | 121 | 116 | 129 |
| 2 | 267 | 220 | 223 | 314 |
| 3 | 343 | 277 | 263 | 326 |
| 4 | 359 | 264 | 275 | 343 |
| 5 | 363 | 260 | 286 | 379 |
| 6 | 347 | 234 | 284 | 381 |
| 7 | 350 | 228 | 280 | 380 |
| 8 | 314 | 215 | 284 | 390 |
| 9 | 317 | 197 | 286 | 387 |
| 10 | 306 | 177 | 275 | 387 |
| 11 | 325 | 156 | 278 | 381 |
| 12 | 316 | 138 | 276 | 390 |
| 13 | 290 | 123 | 278 | 357 |
| 14 | 223 | | 288 | 374 |
| 15 | 173 | | 271 | 390 |
| 16 | 133 | | 254 | 352 |
| 17 | 122 | | 244 | 293 |
| 18 | | | 232 | 200 |
| 19 | | | 191 | 184 |
| 20 | | | 162 | 167 |
| 21 | | | 140 | 147 |
| 22 | | | 131 | 138 |
| 23 | | | 123 | 129 |
| 24 | | | 122 | 126 |
| 25 | | | 117 | |

The invention claimed is:

1. An absorbent product comprising a topsheet, a backsheet, and an absorbent body arranged between a central portion of the topsheet and the backsheet, wherein the topsheet comprises a nonwoven material arranged to be in contact with skin of a user during use of the absorbent product,
    wherein the absorbent product is a panty liner,
    wherein the central portion of a first side of the topsheet faces the absorbent body, the nonwoven material comprises fibres, wherein the fibres, at least on a second side of the topsheet arranged to be in contact with skin of a user during use of the absorbent product, have a coarseness of from 0.1 to 10 dtex, and an outer portion of the absorbent product comprises all regions of the absorbent product that lie beyond an outer periphery of the absorbent body such that, when the absorbent product is being worn, no part of the absorbent body is between the topsheet and the backsheet in the outer portion, wherein the nonwoven material is coated with a lubricating coating composition suitable for use in absorbent, hygiene products and that decreases wettability of the fibres, said lubricating coating composition being present at least on a surface arranged to be in contact with the skin of the user during use of the absorbent product, wherein the lubricating coating composition is provided on the second side of the topsheet only on the outer portion of the absorbent product, wherein the outer portion of the absorbent product consists essentially of the topsheet, the backsheet, the lubricating coating composition, and optionally glue or adhesive.

2. The absorbent according to claim 1, wherein the fibres, at least on the surface arranged to be in contact with skin of the user during use of the absorbent product, have a coarseness of from 0.5 to 3 dtex.

3. The absorbent product according to claim 1, wherein the lubricating coating composition is a silicone oil.

4. The absorbent product according to claim 1, wherein the lubricating coating composition is polydimethylsiloxane.

5. The absorbent product according to claim 1, wherein the lubricating coating composition has a water content less than 5.0 weight percent.

6. The absorbent product according to claim 1, wherein the lubricating coating composition is coated in an amount of 10 ppm to 10%-by weight, based on the total weight of the nonwoven.

7. The absorbent product according to claim 1, wherein the coating is applied by printing or kiss rolling, and wherein the coating is applied to 20-100% of the total surface area of the outer portion.

8. The absorbent product according to claim 1, wherein the nonwoven is spunbond, air laid, wet laid, electro spun, carded or meltblown nonwoven.

9. The absorbent product according to claim 8, wherein the nonwoven comprises spunbond and meltblown nonwoven in a combination and form a layered product spunbond—meltblown—spunbond (SMS) or spunbond-meltdown-meltblown-spunbond (SMMS).

10. The absorbent product according to claim 1, wherein the nonwoven has a basis weight from 8 to 80 g/m$^2$.

11. The absorbent product according to claim 1, wherein the nonwoven comprises absorbent fibres in an amount of 2-10% by weight, based on the total weight of the fibres in the nonwoven material.

12. The absorbent product according to claim 11, wherein the absorbent fibres have a coarseness from 1.1 to 7 dtex.

13. The absorbent product according to claim 1, wherein the nonwoven material has lower friction values in presence of moisture than a nonwoven material comprising fibres and/or nonwoven without a coating with a lubricating coating composition or fibres having a finer coarseness than 0.1 dtex on a surface arranged to be in contact with skin of a user during use of the absorbent product, measured by a curve obtained in repeated runs with measurements according to a method stick and slip described in the description, wherein the friction values in the curve are obtained in repeated runs and wherein the curve comprises a first slope having a positive coefficient illustrating increase in the friction values, a plateau, and a second slope having a negative coefficient illustrating decrease in the friction values.

14. The absorbent product according to claim 1, wherein the fibres include non-absorbent and absorbent fibres, the absorbent fibres being present in an amount of 2-30% by weight.

15. The absorbent according to claim 1, wherein the outer portion of the absorbent product consists of the topsheet, the backsheet, the lubricating coating composition, and optionally glue or adhesive.

16. The method according to claim 15, wherein the outer portion of the absorbent product consists of the topsheet, the backsheet, the lubricating coating composition, and optionally glue or adhesive.

17. A method comprising adding a nonwoven material to an absorbent product comprising a backsheet and an absorbent body arranged between a central portion of the backsheet and the nonwoven material, wherein the nonwoven material is arranged to be in contact with skin of a user during use of the absorbent product to reduce wet friction between the absorbent body and the skin of the user, wherein a first side of the central portion of the nonwoven material faces the absorbent body, wherein the absorbent product is a panty liner, the nonwoven material comprising fibres, wherein the fibres on a second side of the nonwoven material have a coarseness of from 0.1 to 10 dtex, and an outer portion of the absorbent product comprises all regions of the absorbent product that lie beyond an outer periphery of the absorbent body such, when the absorbent product is being worn, no part of the absorbent body is between the topsheet and the backsheet in the outer portion, wherein the nonwoven material is coated with a lubricating coating composition suitable for use in absorbent, hygiene products and that decreases wettability of the fibres, said lubricating coating composition being present at least on the second side arranged to be in contact with the skin of the user during use of the absorbent product, wherein the lubricating coating composition is provided only on the outer portion of the absorbent product, wherein the outer portion of the absorbent product consists essentially of the topsheet, the backsheet, the lubricating coating composition, and optionally glue or adhesive.

18. The method according to claim 17, wherein the nonwoven material is used in substantially non-absorbent regions of the absorbent product.

19. The method according to claim 17, wherein the fibres include non-absorbent and absorbent fibres, the absorbent fibres being present in an amount of 2-30% by weight.

* * * * *